US007427825B2

(12) United States Patent
Frey et al.

(10) Patent No.: US 7,427,825 B2
(45) Date of Patent: Sep. 23, 2008

(54) ELECTRICAL INTERCONNECTIONS AND METHODS FOR MEMBRANE ULTRASOUND TRANSDUCERS

(75) Inventors: Gregg W. Frey, Issaquan, WA (US); Grazyna M. Palczewska, Bellevue, WA (US); Stephen R. Barnes, Bellevue, WA (US); Mirsaid Bolorforosh, Portola Valley, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 718 days.

(21) Appl. No.: 10/799,973

(22) Filed: Mar. 12, 2004

(65) Prior Publication Data

US 2005/0203409 A1 Sep. 15, 2005

(51) Int. Cl.
*H02N 1/04* (2006.01)
*A61B 8/14* (2006.01)

(52) U.S. Cl. ...................................... 310/366; 600/459

(58) Field of Classification Search ................ 600/459; 310/309, 334, 366; 438/42, 53

See application file for complete search history.

(56) References Cited

U.S. PATENT DOCUMENTS 6,359,367 B1 * 3/2002 Sumanaweera et al. ..... 310/309
6,562,650 B2 * 5/2003 Ladabaum .................. 438/53
6,773,401 B1 * 8/2004 Dreschel et al. ............. 600/459
6,831,394 B2 * 12/2004 Baumgartner et al. ....... 310/334
7,087,023 B2 * 8/2006 Daft et al. .................. 600/459
2003/0003221 A1 1/2003 Zhong et al.

* cited by examiner

*Primary Examiner*—Eric F Winakur
*Assistant Examiner*—Michael Rozanski

(57) ABSTRACT

Electrical interconnects are provided for CMUTs. For example, electrodes within the silicon substrate, such as the electrodes at the bottom of the void below membranes, are interconnected together within the substrate. The interconnected electrode may then be used as the grounding electrode. By providing interconnection within the substrate and below the membranes, space for vias and the associated connection between the electrodes on an exposed surface of the substrate is minimized. As another example, an electrical conductor is formed on the side of the silicon substrate rather than the top of the substrate. Conductors on the side may allow routing signals from a top surface to a bottom surface without large wire bonding pads. Alternatively, conductors on the edge provide additional space for wire bonding pads. As yet another example, polymer material used as a matching or protection layer is formed on the top surface of the CMUT with electrical traces routed within the polymer. By using multiple layers of polymer, multiple layers of electrical conductors may be routed without interference.

27 Claims, 1 Drawing Sheet

ELECTRICAL INTERCONNECTIONS AND METHODS FOR MEMBRANE ULTRASOUND TRANSDUCERS

BACKGROUND

The present invention relates to capacitive membrane ultrasonic transducers (CMUTs). In particular, electrical interconnections are provided for CMUTs.

CMUTs typically have a void covered by a membrane. An electrode is positioned on the membrane and another at the base of the void. To generate acoustic energy, an electrically varying signal is applied to one of the electrodes, causing the membrane to flex. To generate electrical energy, the acoustically induced flexing of the membrane generates a differential electrical signal between the two electrodes.

A typical 1D or 2D ultrasound transducer includes hundreds or even thousands of separate transducer elements, each requiring separate signal paths. For a CMUT, a plurality of membranes and associated electrodes may be used together to form a single element. For interconnecting the electrodes for each element to a separate imaging system signal path, a conductor is deposited on a top surface of the CMUT. The electrode in the void may be connected through a via to a conductor on the top surface. The signal traces are then routed or patterned to an edge of the top surface of the CMUT. Wire bonds or flex circuits connect with pads along the edge to complete the interconnection with the imaging system. However, as the density or number of elements increases, such as in a two-dimensional transducer array, the available space for routing electrically isolated traces on a top surface of the CMUT may not be sufficient.

Transistors and other semiconductor devices may be integrated with a CMUT. The integrated electronics are provided below the CMUT, such as in a same semiconductor substrate or a different semiconductor substrate bonded to the CMUT. For electrical interconnection with the electronics, vias are provided from the electrodes of the CMUT through the silicon substrate. To protect digital and analog components, a grounding plane may be formed within the substrate between the CMUT devices and the electronics. U.S. Published Application 2003/0032211 shows one such grounding plane. The grounding plane is patterned to avoid connection with the vias of the electrodes from the CMUT. However, integration of electronics devices and the associated vias for electrical interconnection may add complication to manufacturing, especially where lower cost transducers are desired.

BRIEF SUMMARY

By way of introduction, the preferred embodiments described below include methods and systems for routing electrical signals for CMUTs. For example, electrodes within the silicon substrate, such as the electrodes at the bottom of the void below membranes, are interconnected together within the substrate. The interconnected electrode may then be used as the grounding electrode. By providing interconnection within the substrate and below the membranes, space for vias and the associated connection between the electrodes on an exposed surface of the substrate is minimized. As another example, an electrical conductor is formed on the side of the silicon substrate rather than the top of the substrate. Conductors on the side may allow routing signals from a top surface to a bottom surface without increasing the silicone area for large wire bonding pads. Alternatively, conductors on the edge provide additional space for wire bonding pads. As yet another example, polymer material used as a matching or protection layer is formed on the top surface of the CMUT with electrical traces routed within the polymer. By using multiple layers of polymer, multiple layers of electrical conductors may be routed without interference.

In a first aspect, a membrane ultrasonic transducer is provided for converting between electrical and acoustical energies. A plurality of membranes is supported on a substrate. First and second electrodes are associated with each of the membranes. Electrical interconnections between electrodes of a plurality of the membranes are provided. The electrical interconnections are within the substrate and free of active electronics.

In a second aspect, a method for interconnecting ground electrodes is provided for a capacitive membrane ultrasound transducer. A common electrical interconnection is formed within a semiconductor substrate. A plurality of membranes is formed. The common electrical interconnection is grounded to act as one of at least two electrodes for the membranes.

In a third aspect, a membrane ultrasonic transducer is provided for converting between electrical and acoustical energies. A plurality of membranes is supported on a top side of a substrate. The membranes are grouped into at least two elements. At least one conductive trace is deposited on an edge of the substrate. The conductive trace electrically connects with at least one of the two elements.

In a fourth aspect, a method for electrical routing is provided for a capacitive membrane ultrasound transducer. A membrane having at least one associated electrode is formed. The membrane is on a top surface of a substrate. A conductor is deposited on an edge of the substrate. The conductor electrically connects with the electrode.

In a fifth aspect, a membrane ultrasonic transducer is provided for converting between electrical and acoustical energies. A plurality of membranes is on a substrate. A polymer layer is provided over the plurality of membranes. At least one conductive trace is in the polymer layer.

In a sixth aspect, a method for electrical routing in a capacitive membrane ultrasound transducer is provided. A membrane is formed on a substrate. A polymer layer is formed over the membrane. A conductive trace is deposited on the polymer layer.

The present invention is defined by the following claims and nothing in this section should be taken as a limitation on those claims. Further aspects and advantages of the invention are discussed below in conjunction with the preferred embodiment. The aspects or other features discussed herein or below may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Different electrical connections or interconnections for CMUT transducers are described below. The different techniques may be used together or independently. Other now known or later developed electrical techniques may also be used in conjunction with the techniques described herein. For example, a via may be provided for a grounding connection to electrical interconnections between electrodes within a substrate. As another example, wire bonding is provided on both the top and edge surfaces.

Figure 1:
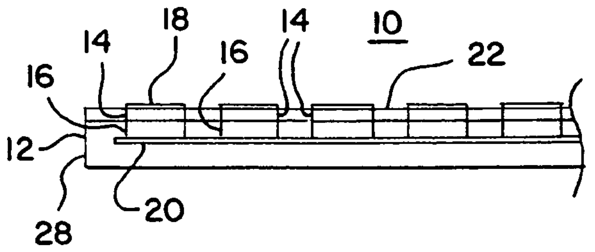
FIG. 1 is a cross-sectional side view of one embodiment of a CMUT with interconnected electrodes.
Figure 3:
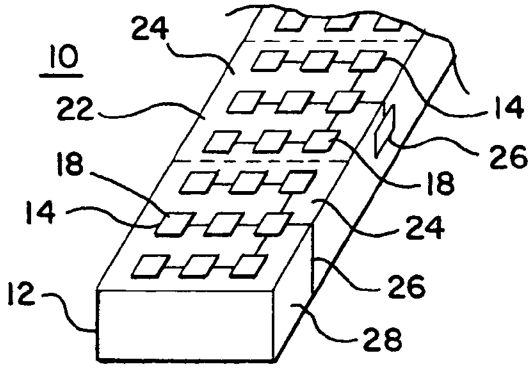
FIG. 3 is a perspective view of one embodiment of a CMUT having conductors on an edge portion.
Figure 5:
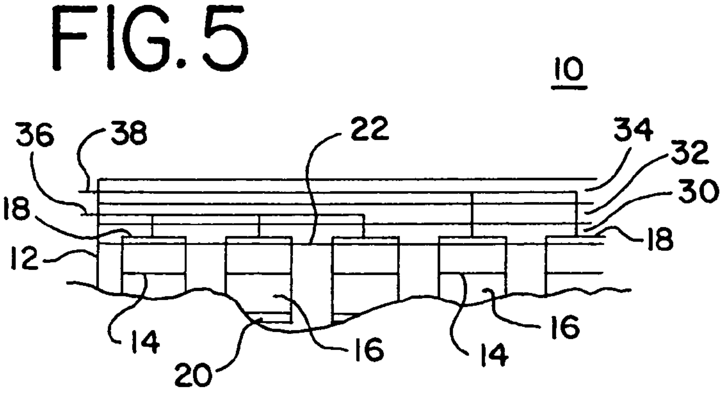
FIG. 5 is a cross-sectional side view of one embodiment of a CMUT transducer with electrical traces routed in polymer layers.

FIGS. 1, 3 and 5 show membrane ultrasonic transducers for converting between electrical and acoustical energies. The membrane ultrasonic transducer 10 is a CMUT in one embodiment. Membrane is used herein broadly to include flexible planks as well as membranes of a drum for transducing between electrical and acoustical energies. The membrane ultrasonic transducer 10 includes a substrate 12, a plurality of membranes 14 disposed over voids 16, the electrodes 18 adjacent to the membranes 14, electrodes 20 adjacent to or within the voids 16, and other now known or later developed CMUT structures. Additional, different or fewer components may be provided.

The substrate 12 is a semiconductor, such as silicon, silicon with layers of additional material, gallium arsenide or other now known or later developed microfabrication materials. The substrate 12 is sized as a rectangular or other shaped slab sufficient to provide a desired number of transducer elements. For example, a linear, narrow slab is provided for a one-dimensional transducer array, and a wide slab is provided for a multi-dimensional transducer array. While additional substrate 12 may be used for signal routing, pads for wire bonding or other structures, the area of the substrate 12 is kept as small as possible.

The membranes 14 are a semiconductor or other material supported on the substrate 12. For example, the membranes 14 are formed as a layer of plasma-enhanced chemical vapor deposition silicon nitride, but any other now known or later developed materials may be used. The membranes are formed through patterning, etching, and use of a sacrificial layer, such as aluminum or a low temperature oxide or glass. By removing the sacrificial layer, the void 16 associated with each membrane 14 is formed. A via with associated etching, photoresist process or other processes is then used to remove the sacrificial layer or portions of the layer remaining after patterning to form the void 16. An additional layer of material is deposited to fill the via in one embodiment, but the via may be unfilled in other embodiments. As shown in FIG. 1, the membranes 14 are on a top surface 22 of the substrate 12. Top surface as used herein includes the membrane layer being exposed on the top surface, the membrane and additional layers deposited over the membranes being exposed on the top surface 22 or other general placement of the membranes 14 to receive acoustic energy from the top surface 22. In alternative embodiments, the membranes 14 are spaced from the top surface, such as by layers of other voids and associated membranes.

As shown in FIG. 3 by the dashed lines, the membranes 14 are grouped into elements 24. While nine membranes 14 are shown for each element of 24 along a linear array in FIG. 3, fewer or greater numbers of membranes 14 may be provided for a given element. For example, as few as one or as many as thousands of membranes may be provided for a single element. A linear distribution of elements is shown in FIG. 3, but a multi-dimensional distribution along square, rectangular, hexagonal, triangular or other grid patterns may be used in other embodiments.

The electrodes 18, 20 for each element 24 may be common for each element 24. For example, the electrodes 18 on a top surface 22 are a metalized layer covering the entire element 24. Alternatively and as shown in FIG. 3, conductors or electrical traces connect each of the separate top electrodes 18 onto a single signal path. Electrodes from different elements may be connected together as a constant reference, such as a connection with ground. Some electrodes 18, 20 are separate or electrically isolated from electrodes 18, 20 from other elements 24.

The electrodes 18, 20 are thin aluminum deposits, but other conductors may be used, such as indium oxide or conductive polymers. Any of sputtering, doping, low temperature deposition or other processes may be used to form the electrodes 18, 20. For example, the electrodes 20 within the void 16 are deposited, etched, patterned or otherwise formed prior to depositing a sacrificial layer for the void 16 and a layer for forming the membranes 14. As another example, the electrodes 18 on the top surface 22 are patterned, deposited and etched or otherwise formed after forming the membranes 14 and before or after removing the sacrificial layer to form the voids 16. Each electrode 18, 20 is associated with a void 16 and membrane 14. As shown in FIG. 1, a common electrode may extend between a plurality of membranes 14 and associated voids 16. At least one electrode of each membrane 14 for a given element 24 is kept separate from an electrode of another element 24. In one embodiment, the top electrodes 18 act as grounding electrodes and may be common to one or more elements, but in other embodiments, the lower electrode 20 operates as the grounding electrode.

For the electrodes 18 forming electrical connections to isolated groups (elements), any now known or later developed connectors may be used for the separate signal traces. For example, a flexible circuit is positioned adjacent to the membranes 14, contacting a signal trace associated with an element to the electrodes 18. Alternatively, the separate signal traces for each element extend to an edge of the substrate 12 on the top surface and terminate at a pad. Wire bonding or connection of the flex circuit to the pads of multiple elements provides electrical connection of separate signal traces for each element 24 to cables or imaging system circuitry. In one embodiment, separate signal traces for elements or electrical connections between electrodes are patterned on the top surface 22. In another embodiment, the conductive signal traces are patterned within or on polymer layers. The deposited conductors form a metalized layer above the membranes 14. To interconnect a plurality of membranes together in a same element or for routing to a side of the top surface 22 for other interconnection, the signal traces extend over a length greater than at least two membranes are wide. Shorter or longer extents may be provided. As an alternative to terminating the separate signal traces on the top surface 22, the traces extend over an edge of the substrate 12 or through vias in the substrate 12. The separate traces either terminate on the edge or extend to the bottom of the substrate 12.

Any now known or later developed technique may be used for forming the CMUT, membranes 14, electrodes 18, 20 and substrate 12. Various CMOS or bipolar processing is used in one embodiment. Using spin deposition, sputter deposition, other forms of deposition, etching, patterning, lapping, evaporating, scribing, photolithographic patterning, or other now known or later developed techniques, the various layers and materials of the CMUT 10 are formed. Semiconductor, insulating and conducting layers are formed as part of the substrate 12.

The formation of the CMUT 10 includes electrical connection or signal traces that minimize semiconductor area on the CMUT 10. In one embodiment, the electrodes are interconnected within the substrate 12. For example, a ground plane of conductive aluminum or other conductor is deposited within the substrate 12. The electrodes 20 are deposited prior to formation to the membranes 14 or depositing and patterning of the sacrificial layer for the void 16. In order to better support the layer for the membranes 14, the electrode layer 20 is patterned or etched to interconnect the electrodes 20 associated with a plurality of membranes within the substrate but still allow contact of the subsequent layers with the layer prior to or below the electrode layer. In alternative embodiments, the electrical interconnection between the electrodes of the plurality of membranes within the substrate 12 is formed by doping the substrate 12. While the electrodes 20 associated with the voids 16 are interconnected as a common grounding electrode or grounding plane in one embodiment, the electrodes on the top surface 18 may be interconnected and used as a grounding electrode in other embodiments. The interconnections within the substrate 12 may be performed in part through vias within the substrate 12 and interconnections within the substrate 12 below the void 16 and the bottom electrodes 20.

The electrical interconnections of the electrode 20 are contained within the bulk of the silicon structure. The electrical interconnections extend between electrodes 20 of different elements 24. By providing the grounding electrode within the bulk of the silicon substrate 12, cross-coupling between elements 24 may be reduced. In alternative embodiments, the electrical interconnection between the electrodes 20 of a single element 24 is isolated from the electrical interconnections of another element 24. The electrical interconnections within the substrate 12 are then connected through a via or other pattern structure to a pad or other connection anywhere on the substrate 12 for connection as a signal trace with an imaging system. Alternatively, the interconnected electrodes 20 within the substrate 12 of each element 24 are then connected together in a common ground through vias, wire bonding or other connections extending at least in part outside or over a surface of the substrate 12. A pad on a substrate connects with the electrically interconnected electrodes for connection to ground or a signal path.

In one embodiment, the electrical interconnections for the electrodes 20 or other common electrodes across multiple membranes 14 within the substrate 12 are free of active electronics. For example, switches, multiplexers or beamforming components are provided within the substrate 12 in some embodiments. For use as a grounding electrode, the electrodes 20 are interconnected without connection to the active electronics of a partial beamformer or other active circuitry within the substrate 12. Alternatively, the electrodes 20 are interconnected within the substrate 12 and a connection external to the substrate 12 is used to connect the electrodes to active electronics. The interconnections are then free of active electronics within the substrate 12.

Figure 2:
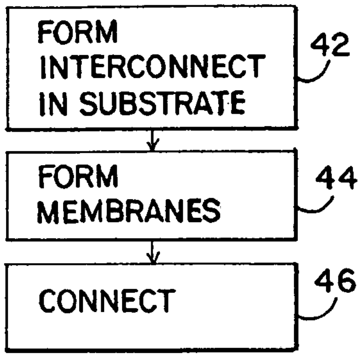
FIG. 2 is a flow chart diagram of one embodiment of a method for interconnecting electrodes.

FIG. 2 shows a flow chart of one embodiment of a method for interconnecting ground electrodes of a capacitive membrane ultrasound transducer. Additional, different or fewer acts may be provided. In other embodiments, the acts are provided in a different order.

In act 42, electrical interconnections are formed within a semiconductor substrate. The substrate is doped in one embodiment. Alternatively, a metal layer is deposited, patterned or etched on the substrate interconnecting across membranes, across elements, or across the entire array. By then depositing additional semiconductor layers, such as for forming the voids or membranes, the electrical interconnections are within the substrate 12.

In act 44, the membranes are formed. Any now known or later developed microfabrication process may be used for forming the membranes. For example, a sacrificial layer is deposited on top of the electrical interconnections. The sacrificial layer is then etched to leave sacrificial material at the locations of desired voids. Silicon or other semiconductor material is then deposited over the sacrificial layer, any exposed electrical interconnections and onto any exposed surfaces of the original substrate. Using vias or other structures, the sacrificial layer is removed, resulting in membranes. The electrical interconnects connect within the substrate below the membranes. For example, the electrical interconnects connect the electrodes associated with the voids of a plurality of membranes. Alternatively, the electrical interconnections within the substrate interconnect electrodes on a bottom or top surface of the membrane.

In act 46, the electrical interconnections are connected to a ground. A permanent or switchable connection may be provided. The connection is provided within the substrate 12 or by routing the interconnections through a via or a pattern to the outside of the substrate 12 and connecting a wire bond, flex circuit or other structure. Each membrane is associated with another electrode as well.

The other electrodes are connected together to form elements. The electrodes of an element are electrically isolated from the electrical interconnections of the grounded electrodes as well as electrical interconnections of electrodes of different elements. The electrodes are connected into electrically isolated groups to form an element. The electrical interconnections are provided within the substrate, on a top surface of the substrate, through vias, or other now known or later developed interconnections.

In another embodiment for use with or without electrical interconnections within a substrate, conductors are deposited or formed on an edge of the substrate as shown in FIG. 3 to conserve space. At least one conductive trace 26 is deposited on the edge of the substrate. The trace is a metal, such as aluminum, but other conductors may be used. In one embodiment, the trace 26 electrically communicates from the top surface 22 to a bottom surface. In another embodiment, the trace 26 on the edge 28 is a pad for wire bonding or other electrical connection. Both alternatives are shown in FIG. 3. Traces 26 extending between elements on an edge may also be used. One, two or three of the alternatives is provided for a given array 10. While shown on a same edge 28, other edges, such as the ends of the array, may be used. By routing the traces along the edge 28, additional real estate or space is provided for electrical interconnection with other devices. Routing on the edge may also avoid vias for performing electrical connections on a bottom surface.

As shown in FIG. 3, each of the traces 26 on the edge is associated with a different element 24. Each electrical trace 26 is electrically isolated from other traces for other elements 24. The trace 26 connects with the electrodes and any other electrical interconnection for an element 24 on the top surface 22. Alternatively, the trace 26 connects with a via on the top surface 22 for electrical connection with electrodes or other signal traces within the substrate 12. In yet another embodiment, metal is exposed on the edge 28 from a conductive layer within the substrate 12. As a result, the trace 26 originates on the edge 28 relative to the outside surface of the substrate 12. For example, the grounding plane formed to interconnect the electrodes 20 of FIG. 1 extends to the edge 28 at one or more locations. A pad or other trace 26 is provided on the edge 28 for connection to ground. In yet another embodiment, the trace 26 on the edge surface 28 connects with electrodes formed in a polymer layer above the surface 22 on a top side of the substrate 12 as discussed below with respect to FIG. 5.

Figure 4:
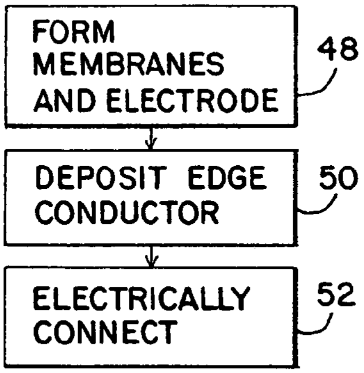
FIG. 4 is a flow chart of one embodiment of a method for forming edge conductors.

FIG. 4 shows a flow chart of one embodiment of a method for electrical routing in a capacitive membrane ultrasound transducer. Additional, different or fewer acts may be provided. A different order for performing the acts may be used.

In act 48, membranes and electrodes are formed. Using CMOS, bipolar or another microfabrication technique, a membrane having at least one electrode associated therewith is formed on a top surface of a substrate. A plurality of membranes and electrodes are formed for use in a transducer array, use in different elements, or use in a same element. Any electrical connections within the substrate 12, such as vias or electrical interconnections on a same layer, as well as electrical interconnections on a top surface 22 or bottom surface of the substrate 12 are formed during manufacture of the CMUT.

In act 50, a conductor is deposited on an edge of the substrate. The substrate is cut or otherwise separated into plates for uses in ultrasound transducer. Alternatively, the substrate begins in a size corresponding to the desired transducer size. After optional plasma etching or other cleaning of the edge surfaces, a metal layer is patterned or deposited onto the edge of the substrate. Using, dicing, scribing, etching or patterning, the metal layer is separated into a plurality of conductors on the edge surface corresponding to different membranes, different elements or other electrically isolated signal traces. Different signal traces may be electrically connected on the edge surface as well. Any now known or later developed semiconductor technique for depositing a signal trace may be used.

In act 52, the conductor on the edge is electrically connected with at least one electrode, such as the common ground electrode or a signal electrode. The electrical connection is provided by depositing the conductor on the edge in a way that connects with conductors on a top surface, bottom surface or within the substrate. For example, the metal layer is deposited and otherwise patterned as if the substrate edge had a greater spatial extent. The deposition of conductor then extends up to and into contact with signal traces on a top surface. The metal layer on the edge is patterned or otherwise etched to form separate signal traces for different electrically isolated elements in one embodiment. The conductors on the edge transmit the electrical signal along the edge, such as a wraparound between the top and bottom surfaces. In another embodiment, the conductor on the edge forms a wire pad. A wire bond is then formed with the conductor for electrical connection away from the substrate.

FIG. 5 shows another embodiment of routing electrical traces for use with a CMUT, such as a CMUT 10 or a multi-dimensional transducer array. One or more layers of polymer or other insulator 30, 32, 34 are formed over the top surface 22 of the substrate 12 and the electrodes 18. Any of various now known or later developed polymers or insulators may be used, such as polymers used to form acoustic matching layers with or without acoustic filler. The polymer layer acts as an insulator as well as an acoustic matching layer. The polymer is deposited using a photoimagable resist, lithographic spinning, CVD or other technique to form thin layers. The layers are built up successively to provide separate electrode pathways. As an alternative to polymer, a semiconductor insulator or other electrically insulating material may be used.

Conductive traces are formed on top of or within the polymer layers 30, 32 and 34. For example, the polymer layer 30 covers the electrodes 18 and any electrical conductive traces formed on a top surface 22 of the substrate 12. An additional layer 32 is then formed or deposited. A conductor 36 is deposited within or under the additional layer 32. For example, the conductor 36 is deposited on top of the layer 30 and then the layer 32 covers the conductor 36, or the layer 32 is etched or otherwise patterned and the conductor 36 is deposited within the pattern. The layers 30 act to insulate each of the conductors 36, 38, 18 from other conductors. Vias may be used for electrical connection to different layers. Any circuit fabrication technique, such as laser scribing, evaporating, sputtering, depositing, lapping or other now known or later developed techniques are used to form the conductive traces within or between the polymer layers. The conductive trace "in" the polymer layer is used herein to indicate a conductive trace entirely within a layer of polymer or on a layer of polymer. As each layer of polymer is deposited, the layer is etched and/or metalized to form the electrical conductive traces. Another layer of polymer is then spun to insulate or provide a new layer for further metalization.

The layer of polymer allows for additional signal traces or conductive traces from one or more electrodes 18 to be electrically isolated from conductive traces of other electrodes 18, such as electrically isolated between elements in a transducer array. In a multi-dimensional array, different polymer layers 30, 32, 34 are used for electrical traces from different elements. The layers allow the conductive trace to extend to a side of the substrate 12 and over or across conductive traces and electrodes associated with different elements. As shown in FIG. 5, the electrical traces 36, 38 extend out of a side of the polymer layers, but may alternatively connect through vias to an upper surface. For example, the polymer layers are deposited such that a stair stepped pattern is provided on the top surface. Conductive pads are formed along each of the stair steps for connection with flex circuits, wire bonds or other electrical connections. Alternatively, vias are provided to the top surface or the bottom surface for electrical connection.

Figure 6:
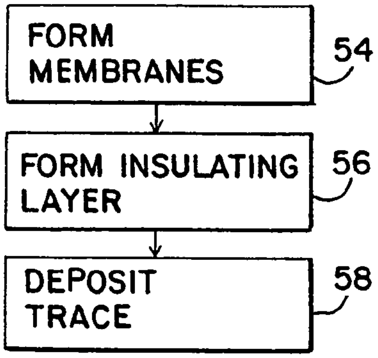
FIG. 6 is a flow chart diagram of one embodiment of a method for routing electrical signals through polymer layers.

FIG. 6 shows a flow chart of one embodiment of a method for electrical routing in a capacitive membrane ultrasound transducer. Additional, different or fewer acts may be provided. The acts may be performed in a different order.

In act 54, membranes are formed on a substrate as discussed above.

In act 56, a polymer layer is formed over the membrane. For example, a polymer layer is lithographically spun to form a thin polymer sheet over the substrate and membranes. A photoimagable overlay or resist or other techniques may be used to form the polymer layer. The polymer layer is formed over any pattern metal layer on an upper surface 22 of the substrate 12. The polymer acts as an insulator. A channel is formed in the polymer layer. For example, the polymer layer is deposited in a pattern with channels. Alternatively, channels are scribed, etched, evaporated or otherwise formed in the polymer layer. The channel is formed such that conductors deposited in the channel avoid contact with other metal layers except where desired, such as through forming a via. In alternative embodiments, a channel is not formed in the polymer layer, but instead a subsequent polymer layer is positioned over a deposited metal layer.

In act 58, a conductive trace is deposited in the polymer layer. For example, a patterned metal layer is formed on a top of a polymer layer. The metal layer is patterned on top of the polymer layer. As an alternative embodiment, the conductive trace is deposited within a previously formed channel. Any excess metal layer is removed by patterning, etching or other techniques. The polymer layer acts to insulate conductive traces from each other. Conductive traces are provided with different layers for extending across the substrate or the transducer array. Conductive traces are isolated from each other for interconnecting elements or electrodes with the desired signal path or ground connections.

Using any of the various routing or electrical connection techniques discussed above, the electrodes associated with membranes or elements are connected to receiver and transmitter electronics. In one embodiment, the receiver electronics are integrated within the same substrate. Alternatively, the receiver electronics are positioned adjacent to the substrate or spaced from the substrate. For example, the receiver electronics are integrated within a separate substrate and bonded to a bottom or side of the substrate used for the CMUT. Electrical connections between the two substrates are then provided using an edge conductor, conductors within the CMUT substrate, conductors within polymer layers above the CMUT substrate, wire bonds, flex circuits or combinations thereof. The interconnections may allow for use of the substrate 12 and CMUT in more confined spaces, such as with a CMUT positioned within a catheter or other transducer for use inside of a body. As an alternative to connection to the receiver electronics, the conductors described above connect with a cable for a remote connection to the electronics. Any of the various techniques described above can be used for either a common or ground electrode configurations or for element-based signal electrode configurations. Additional shielding may be incorporated or integrated into some or all of the layers discussed herein. For example, an electrically separate metal film is connected to ground or allowed to float as an EMI shield within the substrate 12 beneath the bottom electrodes 20.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A membrane ultrasonic transducer for converting between electrical and acoustic energies, the transducer comprising:

a substrate;

a plurality of membranes supported on the substrate;

at least first and second electrodes associated with each of the plurality of membranes;

electrical interconnections between the first electrodes of the plurality of membranes, the electrical interconnections within the substrate and free of active electronics within the substrate;

electrical connections of the second electrodes in at least two electrically isolated groups; and separate signal traces for each of the at least two electrically isolated groups;

wherein the separate signal traces comprises signal traces of a flexible circuit positioned adjacent the membranes.

2. The transducer of claim 1 further comprising:

a first pad on the substrate connected with the electrical interconnections;

wherein the first electrodes correspond to at least two elements of the transducer.

3. The transducer of claim 1 wherein the separate signal traces comprise conductive material deposited on an edge of the substrate, the membranes being on a top of the substrate.

4. The transducer of claim 1 wherein the separate signal traces comprise deposited conductors in a layer above the membranes, the deposited conductors extending over a length greater than at least two membranes.

5. The transducer of claim 1 wherein the electrical interconnections comprise a grounding plane.

6. A method for interconnecting ground electrodes of a capacitive membrane ultrasound transducer, the method comprising:

(a) forming a common electrical interconnection within a semiconductor substrate;

(b) forming a plurality of membranes associated with the electrical interconnection as one of at least two electrodes;

(c) grounding the common electrical interconnection;

(d) forming electrodes electrically isolated from the electrical interconnection;

(e) connecting the electrodes into at least two groups, each group electrically isolated the other groups; and (f) positioning a flexible circuit adjacent the membranes and electrodes of the at least two groups.

7. The method of claim 6 wherein (c) comprises connecting the electrical interconnection to ground without active electronics.

8. A membrane ultrasonic transducer for converting between electrical and acoustic energies, the transducer comprising:

a substrate;

a plurality of membranes supported on a top side of the substrate, the plurality of membranes grouped into at least two elements; and at least one conductive trace deposited on an edge surface of the substrate, the edge surface being a side of the substrate adjacent to and different than the top side of the substrate, the at least one conductive trace electrically connected with at least one of the at least two elements;

wherein the at least one conductive trace comprise pads on the edge surface.

9. The transducer of claim 8 wherein the at least one conductive trace comprises at least two conductive traces electrically isolated from each other, the at least two conductive traces corresponding to the at least two elements, respectively.

10. The transducer of claim 8 wherein the at least one conductive trace connects a trace on the top of the substrate to a trace on a bottom of the substrate.

11. The transducer of claim 8 further comprising:

electrical interconnections within the substrate, the electrical interconnections common to the at least two elements.

12. The transducer of claim 8 wherein the at least one conductive trace connects with a trace on the top of the substrate, the trace on the top of the substrate formed in a polymer layer above the plurality of membranes.

13. A method for electrical routing in a capacitive membrane ultrasound transducer, the method comprising:

(a) forming a membrane having at least one electrode, the membrane being on a top surface of a substrate;

(b) depositing a pad conductor on an edge of the substrate, the edge being a side of the substrate adjacent to and different than the top surface of the substrate; and (c) electrically connecting the conductor with the at least one electrode.

14. The method of claim 13 wherein (a) comprises forming the membrane and additional membranes each having at least one electrode; wherein (b) comprises depositing the conductor and additional conductors on the edge; and wherein (c) comprises electrically connecting the at least one electrode of each additional membrane to respective additional conductors on the edge, each electrical connection associated with an electrically isolated element.

15. The method of claim 13 wherein (b) comprises:

(b1) depositing a metal layer on the edge; and (b2) separating the metal layer into a plurality of conductors.

16. The method of claim 13 further comprising:

(d) wire bonding to the conductor.

17. A membrane ultrasonic transducer for converting between electrical and acoustic energies, the transducer comprising:

a substrate;

a plurality of membranes on the substrate;

a polymer layer over the plurality of membranes; and at least one conductive trace in the polymer layer.

18. The transducer of claim 17 further comprising:

an additional polymer layer over the plurality of membranes; and an additional conductor electrically isolated from the at least one conductive trace, the additional conductor being within the additional polymer layer.

19. The transducer of claim 17 wherein the at least one conductive trace comprises a plurality of conductive traces deposited partially on a top surface of the substrate, where the polymer layer covers and is between the plurality Of conductive traces.

20. The transducer of claim 17 wherein the polymer layer includes polymer between the at least one conductive trace and a top surface of the substrate.

21. The transducer of claim 17 further comprising:

at least one conductor deposited on an edge of the substrate, the polymer layer being on a top of the substrate, the at least one conductor electrically connected with the at least one conductive trace.

22. The transducer of claim 17 wherein the plurality of membranes comprise at least two elements, the at least one conductive trace comprising a conductive trace for each of the at least two elements, each conductive trace electrically isolated for the other conductive traces.

23. The transducer of claim 17 wherein the plurality of membranes comprise at least two elements;

further comprising:

electrical interconnections within the substrate, the electrical interconnections common to the at least two elements.

24. A method for electrical routing in a capacitive membrane ultrasound transducer, the method comprising:

(a) forming a membrane on a substrate;

(b) depositing an insulating layer over the membrane; and (c) depositing a conductive trace on the insulating layer.

25. The method of claim 24 wherein (c) comprises patterning a metal layer.

26. The method of claim 24 further comprising:

(d) forming a channel in the insulating layer;

wherein (c) comprises depositing the conductive trace in the channel.

27. The method of claim 24 wherein (b) and (c) comprise creating a plurality of conductive traces in different insulating layers, each of the plurality of conductive traces electrically isolated from the other conductive traces.

* * * * *